United States Patent [19]

Haferkorn

[11] 4,252,545

[45] Feb. 24, 1981

[54] PROCESS FOR THE FRACTIONAL DESUBLIMATION OF PYROMELLITIC ACID DIANHYDRIDE

[75] Inventor: Herbert Haferkorn, Bottrop, Fed. Rep. of Germany

[73] Assignee: Chemische Werke Huls AG, Herne, Fed. Rep. of Germany

[21] Appl. No.: 961,561

[22] Filed: Nov. 17, 1978

[30] Foreign Application Priority Data

Nov. 22, 1977 [DE] Fed. Rep. of Germany ....... 2751979

[51] Int. Cl.$^3$ .............................................. B01D 7/02
[52] U.S. Cl. ........................................ 55/82; 260/707
[58] Field of Search .................... 55/82; 23/294 R; 422/244; 260/706, 707, DIG. 35

[56] References Cited

U.S. PATENT DOCUMENTS

| 3,609,943 | 10/1971 | Richter | 55/82 |
| 4,036,594 | 7/1977 | Ibing et al. | 55/82 |

Primary Examiner—Hiram H. Bernstein
Attorney, Agent, or Firm—Oblon, Fisher, Spivak, McClelland & Maier

[57] ABSTRACT

A process for the fractional desublimation of pyromellitic acid dianhydride in the form of free-flowing crystals which comprises reducing a reaction gas containing pyromellitic acid dianhydride produced by a chemical reaction which also produces by-products, to a temperature above the thaw point of the by-products but below the desublimation point of pyromellitic acid dianhydride by means of a smooth thermostaticized cooling surface, directing the reaction gases at maximal flow velocities of 3 m/sec parallelly to the cooling surface and separating the fraction of crystals not adhering to the surface.

11 Claims, 1 Drawing Figure

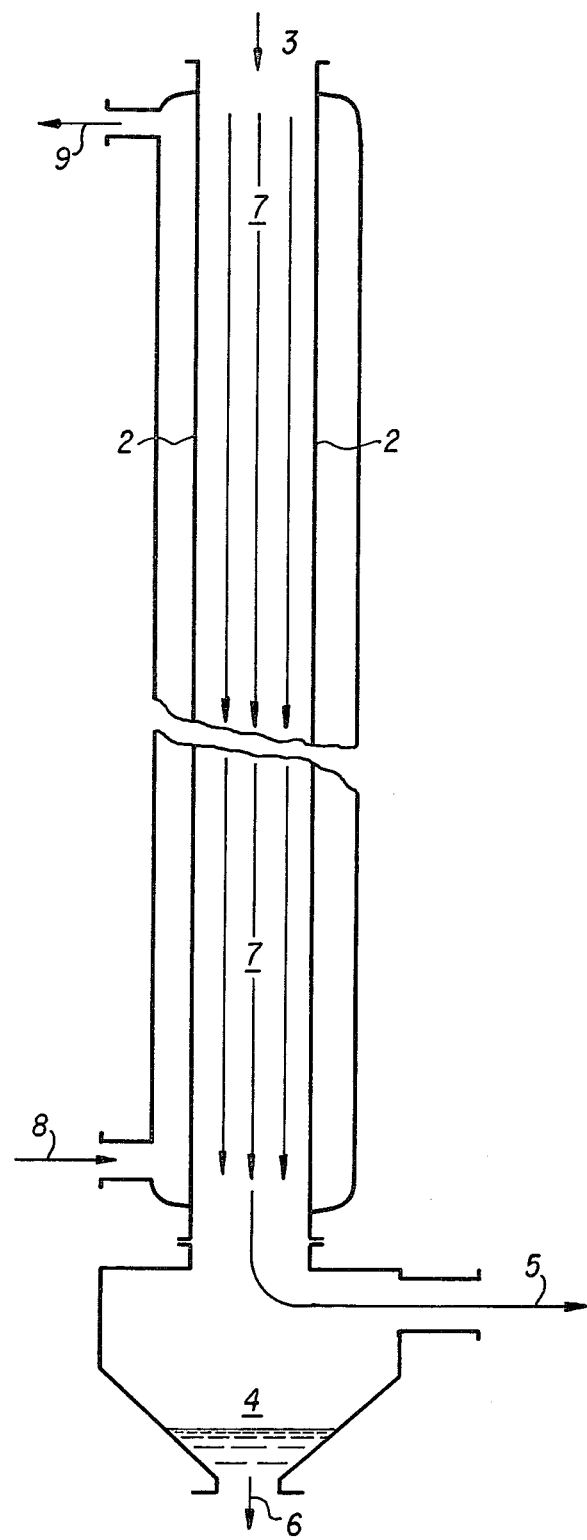

PROCESS FOR THE FRACTIONAL DESUBLIMATION OF PYROMELLITIC ACID DIANHYDRIDE

BACKGROUND OF THE INVENTION

1. Field of the Invention

The present invention relates to a process for the fractional desublimation of pyromellitic acid dianhydride.

2. Description of the Prior Art

The economical preparation of very pure, sublimable, organic substances, i.e., such substances which, under working conditions, change directly from the vaporous to the solid state, from a hot gas mixture which is mainly taken from a reactor for the preparation of said substances and which, as an impurity, contains by-products which, under the required working conditions, remain in the form of vapor, has gained significance during the past few years.

The separation of sublimable substances from gas mixtures containing them, is known. All these known processes have the joint requirement that the hot gas be cooled on cooled surfaces to such an extent that the desired degree of separation is reached for the substance to be obtained. Here, the heat exchanger surfaces usually become coated with the product so that a periodic removal is necessary. Large-volume sublimation chambers can be emptied easily by means of scrapers and brushes. However, because of the relatively small chamber surfaces, the throughput or the space-time yield is small. The presently most economical separators are ribbed pipe condensers which, however, cannot be emptied mechanically. In this case, the sublimate or the condensate is obtained by a periodic heating of the ribbed pipes to temperatures above the solidification point of the obtained products and by the drainage of the products into collectors. The disadvantage of this process is the requirement that two condensers have to be operated alternately, one of which is loaded, while the other one is melted off. In addition, such a condenser is useless for products which have a very high melting point and/or decompose at their melting point. Among the products that cannot be obtained in ribbed pipe condensers of conventional construction is, among other products, pyromellitic acid dianhydride (PMDA). First, the melting point at 285° C. is so high that a melting off would present technical difficulties, and secondly, the product will discolor when the PMDA is heated to melting temperature. This discoloration cannot be eliminated by means of the methods known up to date, unless distillation is carried out which, because of the high melting point of the product, also presents considerable technical problems.

Several known processes are indicated in literature concerning the separation of PMDA from reaction gases:

Thus the use of sublimation chambers was suggested several times, in which case, in order to improve effectiveness, cooling surfaces and baffle plates may be installed, or a cooling of the gases is carried out by injecting water, in which case the cooling must, however not exceed 555° C./sec. The disadvantage of the latter process is the increase of the thaw point of the water, which results in an increased formation of pyromellitic acid (PMS). The mixing of the hot reaction gases with cold air seems to have a more favorable effect. However, this method results in fine crystals which, because of the increase in flow speed, are increasingly discharged from the sublimation chambers. In order to avoid such losses, filter or water washes have been suggested.

The water wash of all reaction gases is much simpler. In this case, the whole product accumulates as PMS which then, according to various methods must again be dehydrated into dianhydride.

According to another process, the hot reaction gases which contain PMDA, are brought in contact with pneumatically transported solid balls which absorb the heat and thus coat themselves with the material to be sublimated. In a separate facility, the solid balls are cleaned (baffle effect) and cooled mechanically before they are transported back into the sublimation chamber. Understandably, this process requires complicated equipment.

It is also known that the PMDA accumulating as a result of the gas phase oxidation of tetra-alkylated benzene (for example, durene) is rendered impure through a number of by-products, the vapor pressures of which are higher than that of the PMDA and/or, because of their more extensive dilution in the reaction gas, have a lower thaw point. Among these are: Trimellitic acid anhydride, dimethyl-, monomethyl-phthalic acid anhydride and phthalic acid anhydride as colorless impurity in addition to a number of other dark-colored compounds. In order to remove these impurities, refining is required. The suggested processes usually deal with a treatment of the crude product with solvents, especially ketones or solvent mixtures, while another process became known in which hot inert gas or air, at temperatures between 100° and 200° C., at a quantity of 1 to 150 kg gas/kg crude PMDA is directed over or through the crude product, until a degree of purity of 99% is reached.

It is also known that pure PMDA can be obtained when the desublimation of the crude product is carried out at temperatures between 130° and 200° C.

In a newer process, PMDA-containing reaction gases, which were precooled to a temperature which is 5°–10° C. above the thaw point of the PMDA, are directed vertically through a thermostatized, perforated cooling surface, which makes it possible to cool the gases to a temperature above the thaw point of the by-products, in which case, pure PMDA accumulates on the flow-in side of the cooling surface. This pure PMDA can be easily separated mechanically. However, apparatuses of this type can only be set up for a large-scale PMDA preparation with the expenditure of considerable costs.

SUMMARY OF THE INVENTION

This invention provides a process for the fractional desublimation of pryomellitic acid dianhydride in the form of free-flowing crystals which comprises bringing a reaction gas containing pyromellitic acid dianhydride derived from a reaction which also produces by-products, to a temperature above the thaw point of said by-products by means of a smooth thermostaticized cooling surface, directing the reaction gases at maximal flow velocities of 3 m/sec parallelly to said surface and separating the fraction of crystals not adhering to said surface from the fraction adhering to said surface.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawing wherein:

The FIGURE shows a cross-sectional view of the thermostatized PMDA desublimator described in Example 1.

DESCRIPTION OF THE PREFERRED EMBODIMENTS

It was now found that during the passage of the PMDA-containing reaction gases which were pre-cooled to 5°–10° C. above the thaw point for PMDA but below the desublimation point of PMDA through thermostatized pipes, in which case a cooling of the gases to a temperature above the thaw point of the present impurities is reached, the PMDA that is to be desublimated, partly adheres to the wall of the pipe, while another part leaves the pipe as crystal with the cooled gas current and can be separated according to the known methods (cyclone, filter).

Surprisingly, it was found that the ratio of the adhering crystals to the discharged crystals will increase with the rise of the flow velocity of the gases through the pipe. This means that, in the case of low flow velocities, a significant part of the PMDA crystals to be desublimated can be obtained in the outlet-connected collector space and can be drawn off as a free-flowing crystalline product of high purity.

The result of the invention is therefore a process for the fractional desublimation of highly pure pyromellitic acid dianhydride from reaction gases containing it, in the form of free-flowing crystals, in which case the reaction gases, which were precooled in a known manner, are, for the purpose of further cooling, known by itself, brought to temperatures above the thaw point of the by-products, wherein the reaction gases, at low flow velocities of maximally 3 m/sec., in particular, maximally 1 m/sec., are directed parallel to thermostatized smooth-surface cooling surfaces.

The crystals that adhere in the pipe must be removed periodically according to known methods (washing with water, lye or solvent, mechanical removal or melting off). A low flow velocity is a velocity at which the gases flow through the pipe in as laminar a fashion as possible. The firmly adhering part of the accumulating PMDA crystals in the pipe can thus be lowered under 20% of the total accumulation.

The fact that especially low flow velocities affect the separation ratio in the above-mentioned way, is unexpected. One would rather expect the prevention of adhesions at high gas velocities, because they result in a mechanical friction effect on the wall.

In addition to the fact of the smaller portion of adhering crystal deposits in the pipe—compared with the loosely accumulating crystals—the operation using a slower flow velocity results in the formation of larger crystals which can be more easily separated in the outlet-connected apparatuses (cyclone, filter).

Similar observations were also made when—as mentioned above- pre-cooled PMDA-containing reaction gases are led along differently constructed thermostatized cooling surfaces (for example, plate coolers). In the case of the laminar flow of the gases parallel to the cooling surface-if the cooling of the gases is assured—pure PMDA accumulates in well-formed crystals, which can easily be separated, whereas deposits on the cooling plates occur only in smaller quantities over an extended period of time. In the case of high gas velocities, deposits can be increasingly observed also on cooling surfaces of that type.

Having generally described this invention, a further understanding can be obtained by reference to certain specific examples which are provided herein for purposes of illustration only and are not intended to be limiting unless otherwise specified.

EXAMPLE 1

A reaction gas is present originating from a reaction kiln, for the catalytic oxidation of isopropylpseudocumene (IPPC). This reaction gas, at 430° C., contains 4.7 g PMDA in addition to 0.9–1.2 g impurities per $Nm^3$. In the case of this gas the thaw point for PMDA is at about 200° C. For the testing of the desublimators, a partial current is taken from this gas and precooled to 210°–220° C. (at this temperature, there is still no desublimation).

37 $Nm^3$/hrs. of this reaction gas are directed downward through a vertically arranged 6 m long double-casing pipe made of V4A-steel with 46 mm inside diameter, which by means of oil circulation, is thermostatized to 130° C. Cooled to about 150° C., it enters a separating space with outlet-connected filter arranged below the pipe. The average flow velocity in the pipe is about 10 m/sec. After a period of $47\frac{1}{2}$ hours, 1757 $Nm^3$ reaction gas have passed through. There is a notable pressure loss in the pipe. 2.5 kg PMDA of high purity (99.8%) are discharged from the collector space and the filter. 5.0 kg PMDA remain in the desublimation pipe forming a hard, tightly packed coating which adheres firmly to the wall of the pipe. The quantity remaining in the desublimation pipe amounts to 67% of the total quantity which can be obtained by desublimation from the reaction gas. It is removed by washing with hot water.

The figure shows the embodiment of the thermostatized device mentioned above wherein desublimator 1 is a double casing pipe having inner thermostatized cooling surfaces 2. Reaction gas enters the desublimator 1 at 3 and the cooled gas exits the device at 5. The PMDA crystals which are discharged from the device are collected in space 4 and removed at opening 6. The laminar flow of reaction gas through desublimator 1 is shown by lines 7. Oil to cool desublimator 1 and regulate its temperature enters at opening 8 and exits at opening 9.

EXAMPLE 2

9.7 $Nm^3$/hour of the same reaction gas are directed through the apparatus of example 1. The average flow velocity in the pipe is 2.7 m/sec. 2250 $Nm^3$ had passed through after 232 hours. There was a similar loss of pressure as in example 1. 5.9 kg PMDA (99.8% purity) are obtained from the collecting space and the filter. 3.8 kg product remain as coating in the desublimation pipe. In comparison to the coatings of Example 1, a slightly lower firmness can now be observed.

39% of the total product remain in the desublimation pipe.

EXAMPLE 3

3.6 $Nm^3$/hour of the reaction gas are directed through the apparatus of Example 1. The average flow speed is about 1 m/sec. 1475 Nm³ of the reaction gas passed through in 410 hours. A fall of the pressure decrease in the pipe cannot be observed. 4.7 kg PMDA (purity 99.9%) are obtained from the collector space and filter. 1.6 kg remain in the desublimation pipe, which deposit at the wall of the pipe as a very loose coating. It consists of interlocked coarse crystals which can be easily removed from the wall.

25% of the total product remain in the desublimation pipe.

EXAMPLE 4

Instead of the double-casing pipe with 46 mm inside diameter (Example 1-3), a double-casing pipe made of V4A-steel with 100 mm inside diameter is used. This pipe is charged with 16.1 Nm³/hour of the above-listed reactions gases. The temperatures are adapted to the preliminary tests. The average flow velocity is 1 m sec. 7832 Nm³ passed through over a period of 487 hours. There is no pressure gradient in the pipe. During the whole period of operation, an approximately 15 mm thick layer was loosely deposited on the wall of the pipe, which during the cooling, at the end of the test, partly falls off. 30.3 kg PMDA (purity 99.8%) are obtained from the collector space and the filter. Another 3.1 kg (=9.3% of the total quantity) are removed from the apparatus by washing with water.

EXAMPLE 5

A reaction current of 66 Nm³/hour is directed vertically downward through a plate cooler with 7.5 m² effective cooling surface, plate distance 120 mm, plate length 1000 mm. With a free-space sectional area of the cooler of 0.4 m² and an average gas temperature of 175° C. (entrance temperature 200° C.; exit temperature 150° C., with a temperature at the cooling plate of 130° C.), the average flow velocity is 7.5 cm/sec.

The test is terminated after 562 hours of operating time. 149.8 kg PMDA (purity 99.8%) accumulated, which can easily be removed from the collector space. On the cooling plate there is a loose coating of about 3-4 mm, which is washed off. This is 6.75 kg PMDA (purity 99.6%), which is 4.3% of the total accumulation.

Having now fully described this invention, it will be apparent to one of ordinary skill in the art that many changes and modifications can be made thereto without departing from the spirit or scope of the invention set forth herein.

What is claimed as new and intended to be covered by letters patent is:

1. A process for the fractional desublimation of pyromellitic acid dianhydride in the form of free flowing crystals, which comprises:
   bringing a reaction gas containing pyromellitic acid dianhydride derived from a reaction which also produces by-products to a temperature above the thaw point of said by-products by means of a smooth thermostaticized cooling surface;
   directing the reaction gas at maximal flow velocities of 3 m/sec parallel to said smooth surface which maintains essentially laminar flow conditions of said reaction gas; and
   separating the fraction of crystals not adhering to said surface from the fraction adhering to said surface.

2. Process according to claim 1, wherein said reaction gases are led vertically downward through the pipes of said thermostatized pipe assembly.

3. Process according to claim 1, wherein said reaction gases are directed parallel to the heat exchange surfaces of a plate cooler.

4. A process according to claim 1 wherein the maximal flow velocity of said gas is 1 m/sec.

5. The process of claim 1 wherein the crystalline fraction not adhering to said surface is collected by means of a filter.

6. The process of claim 1 wherein the crystalline fraction not adhering to said surface is collected by means of a cyclone.

7. The process of claim 1 wherein the crystalline fraction adhering to said surface represents less than 20% of the total accumulation of crystals.

8. The process of claim 1 wherein the purity of the crystals not adhering to said surface is better than 99.8%.

9. The process of claim 1 wherein said trimellitic acid dianhydride is obtained from the gas phase oxidation of an alkylated benzene, and wherein said by-products are trimellitic acid anhydride, dimethylnaphthylic acid dianhydride, or monomethylnaphthylic acid dianhydride, or mixtures thereof.

10. The process of claim 9 wherein said alkylated benzene is durene.

11. The process of claim 9 wherein said alkylated benzene is isopropyl pseudocumene.

* * * * *